(12) United States Patent
Voth et al.

(10) Patent No.: US 11,969,261 B1
(45) Date of Patent: Apr. 30, 2024

(54) METHOD AND SYSTEM FOR MODIFYING CONTACT STATUS OF AN ELECTRODE

(71) Applicant: St. Jude Medical, Cardiology Division, Inc., St. Paul, MN (US)

(72) Inventors: Eric J. Voth, Maplewood, MN (US); Jeffrey A. Schweitzer, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 18/096,200

(22) Filed: Jan. 12, 2023

(51) Int. Cl.
*A61B 5/00* (2006.01)

(52) U.S. Cl.
CPC .................. *A61B 5/6844* (2013.01)

(58) Field of Classification Search
CPC .................................... A61B 5/6844
USPC ........................................ 324/650
See application file for complete search history.

(56) References Cited

U.S. PATENT DOCUMENTS

| | | | |
|---|---|---|---|
| 10,188,314 B2 | 1/2019 | Mosesov et al. | |
| 10,398,348 B2 | 9/2019 | Osadchy et al. | |
| 10,750,974 B2 | 8/2020 | Curran | |
| 10,799,148 B2 | 10/2020 | Mosesov et al. | |
| 11,179,194 B2 * | 11/2021 | Sliwa | A61B 18/1492 |
| 11,439,319 B2 | 9/2022 | Curran | |
| 11,612,334 B2 | 3/2023 | Mosesov et al. | |
| 11,612,335 B2 | 3/2023 | Mosesov et al. | |
| 2015/0196215 A1 | 7/2015 | Laughner et al. | |
| 2017/0348049 A1 | 12/2017 | Vrba et al. | |
| 2019/0183378 A1 * | 6/2019 | Mosesov | A61B 5/6852 |
| 2019/0274581 A1 | 9/2019 | Mosesov et al. | |
| 2022/0192604 A1 | 6/2022 | Palti et al. | |
| 2023/0077196 A1 | 3/2023 | Curran | |

OTHER PUBLICATIONS

Extended European Search Report Mailed on Feb. 15, 2024, for Application No. 23214178.8, 16 Pages.
Janin, Jager , et al., "Reconstruction of electroencephalographic data using radial basis functions", Clinical Neurophysiology, Elsevier, Amsterdam, NL, vol. 127, No. 4, Jan. 25, 2016 (Jan. 25, 2016), pp. 1978-1983, X P029460948, ISSN: 1388-2457, DOI: 10.1016/J. CLINPH.2016.01 .003.

* cited by examiner

*Primary Examiner* — Farhana A Hoque
(74) *Attorney, Agent, or Firm* — Billion & Armitage

(57) ABSTRACT

A method of modifying contact status of one or more electrodes in a plurality of electrodes located on a medical device includes measuring an electrical characteristic of each electrode in the plurality of electrodes located on the medical device, determining a contact status for each electrode in the plurality of electrodes based on the measured electrical characteristic for the corresponding electrode, wherein the contact status is indicative of contact with adjacent tissue. The method further includes modifying the contact status of a first electrode in the plurality of electrodes based on the determined contact status of one or more other electrodes in the plurality of electrodes.

20 Claims, 12 Drawing Sheets

Initial Status

Modified Status

Initial Status

Modified Status

Initial Status

Modified Status

Initial Status

Modified Status

Initial Status

Modified Status

Initial Status

Modified Status

METHOD AND SYSTEM FOR MODIFYING CONTACT STATUS OF AN ELECTRODE

TECHNICAL FIELD

The present invention relates generally to medical devices and systems and methods of detecting contact between electrodes on the medical device and adjacent tissue based on measured impedances.

BACKGROUND

Catheters are utilized in a number of operations within the human body. In many of these applications, whether collecting data from surrounding tissue or administering treatment, it is important to determine the proximity of the catheter—in particular the electrodes collecting data or administering treatment—with the adjacent tissue. A number of methods are utilized to make this determination, including for example monitoring electrocardiogram signals (e.g., voltage measured between electrodes) and/or impedance of an electrode. For example, impedance is understood, in general, to increase in response to contact with tissue. However, a number of other factors may also result in variations in impedance, including location of the electrode within the body (i.e., different chambers of the heart, exposed to different volumes of blood flow, may exhibit different impedance values) and movement of the surrounding tissue as a result of, for example, heartbeats. These factors may make it difficult to rely solely on impedance measurements for a particular electrode in deciding whether that electrode is in contact with tissue. Moreover, such limited reliance ignores measurements or other relevant information from nearby electrodes. It would therefore be beneficial to develop a method of modifying the status of a 'no contact' electrode based on collected data of neighboring electrodes.

SUMMARY

According to one aspect, a method of modifying contact status of one or more electrodes in a plurality of electrodes located on a medical device includes measuring an electrical characteristic of each electrode in the plurality of electrodes located on the medical device, determining a contact status for each electrode in the plurality of electrodes based on the measured electrical characteristic for the corresponding electrode, wherein the contact status is indicative of contact with adjacent tissue. The method further includes modifying the contact status of a first electrode in the plurality of electrodes based on the determined contact status of one or more other electrodes in the plurality of electrodes.

According to another aspect, a method of modifying contact status of one or more electrodes in a plurality of electrodes located on a medical device includes measuring an electrical characteristic of each electrode in the plurality of electrodes located on the medical device, determining a contact status for each electrode in the plurality of electrodes based on the measured electrical characteristic for the corresponding electrode, the contact status comprising 'in contact', 'intermittent contact' and 'no contact', and modifying the contact status of one or more electrodes in the plurality of electrodes based on one or more neighboring electrodes having a contact status of 'in contact'.

According to another aspect, a system for use with a medical device having a plurality of electrodes and configured for insertion within a patient includes a signal generator configured to apply a plurality of drive signals across different pairs of electrodes of the medical device, a measurement circuit configured to measure responses of the plurality of electrodes to the drive signals and generate an impedance value for each of the plurality of electrodes of the medical device, and a contact assessment module configured to, for each electrode, determine a contact status of each of the plurality of electrodes based on the generated impedance value associated with each electrode, wherein the contact assessment module is further configured to modify the contact status of one or more of the plurality of electrodes based, at least in part, on the contact status of one or more neighboring electrodes.

DETAILED DESCRIPTION

According to some embodiments, the claimed invention utilizes the contact status of neighboring electrodes to modify the contact status of one or more electrodes. The contact state or status of each of the electrodes is determined by a measured electrical characteristic, such as, for example, a bipolar electrode complex impedance (BECI) measurement. For example, the contact status of an electrode in the most basic example is either 'in contact' or 'not in contact' with the adjacent tissue. In some embodiments, electrodes assigned a contact status of 'not in contact' or 'no contact' is changed to indicate contact with the tissue based on neighboring electrodes being identified as 'in contact' with the adjacent tissue.

As used herein the term 'adjacent' refers to electrodes that do not include another electrode located between them. Adjacent electrodes may be located on the same spline as one another or on different splines so long as no other electrode is located between them.

As used herein the terms 'neighbor', 'neighbors' and 'neighboring' refer to electrodes that are adjacent to one another, as well as electrodes that are separated from one another by one or more other electrodes (non-adjacent). As used herein the term 'nearest neighbor' refers to electrodes directly adjacent to each other with no other electrode located between them.

As used herein the term 'clique' refers to sub-sets of two or more electrodes. An electrode may be associated with more than one clique. For example, a clique may include a group of three electrodes, wherein each electrode in the clique may be a part of other cliques.

Figure 1:
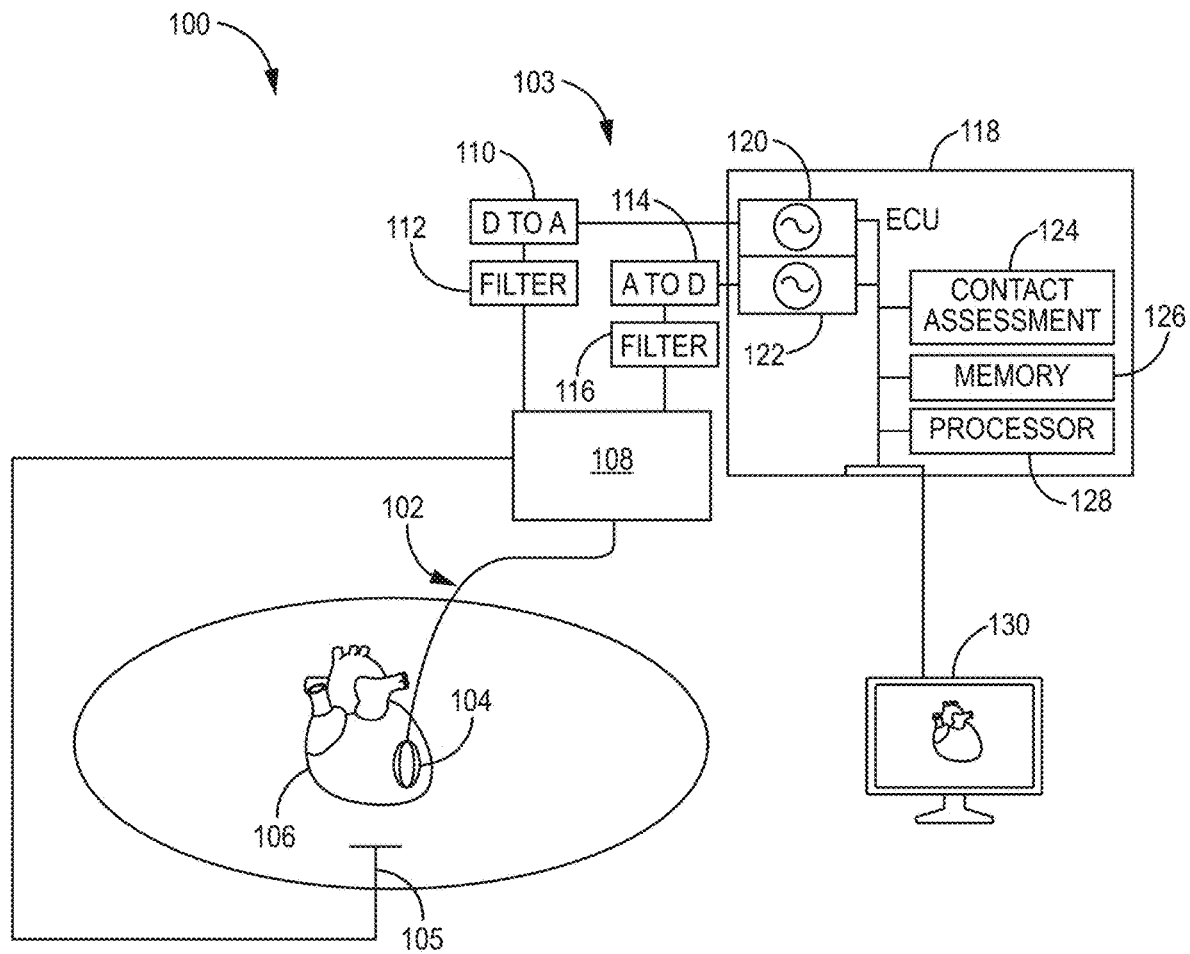
FIG. 1 is a diagrammatic depiction of a system including a medical device for insertion within a patient, the system configured to utilize measured bipolar electrode complex impedances between electrodes to determine contact status of the one or more electrodes located at a distal end of the medical device according to some embodiments.

FIG. 1 is a diagrammatic depiction of a system 100 including a medical device 102 and a local system 103. In some embodiments, the local system includes a switch 108, a digital-to-analog (D to A) converter 110, a filter 112, an analog-to-digital (A to D) converter 114, a filter 116, a display 130, and an electronic control unit (ECU) 118 that may include a signal source 120, a synchronous demodulator circuit 122, a contact assessment module 124, a memory 126, and a processor 128. In some embodiments, one or more surface patch electrodes 105 may be adhered to the skin of the patient.

In some embodiments, the medical device 102 is an elongate medical device, such as a diagnostic and/or therapy catheter, an introducer, sheath, or other similar type of device. The medical device 102 includes a distal end 104 and a proximal end (not shown) that includes a handle operated by a technician as well as interfaces for interfacing the medical device 102 to the local system 103. The distal end 104 may include various sensors and/or components for localization/navigation of the distal end 104 within the patient, mapping of physiological parameters within the patient, and delivery of therapy. In particular, the distal end 104 of the medical device includes a plurality of electrodes that may be utilized for one or more of these purposes.

In some embodiments, contact status of the one or more electrodes located at the distal end 104 of the medical device 102 is determined based on one or more electrical characteristics measured at the electrode. For example, in some embodiments the measured electrical characteristic is a bipolar electrode complex impedance (BECI) generated by driving an excitation signal between two electrodes forming a bipolar pair. The resulting voltage at each of the electrodes is measured and utilized to derive a complex impedance signal. In some embodiments, contact assessment module 124 utilizes the BECI measurements, either alone or in combination with other measured electrical characteristics, to determine contact status of each electrode. In some embodiments, the term "contact status" is a binary determination, with the electrode either being "in contact" with the tissue or "not in contact" with the tissue. In other embodiments, the term "contact status" may include additional contact states, such as "intermittent contact". In still other embodiments, the term "contact status" may describe a proximity of the electrode to adjacent tissue.

In the embodiment shown in FIG. 1, signal source 120 is utilized to generate the excitation signal. In some embodiments, signal source 120 generates one or more excitation or drive signals, each at a unique frequency. More specifically, the signal generator 120 may generate a plurality of excitation or drive signals having unique frequencies within a range from about 1 kHz to over 500 kHz, more typically within a range of about 2 kHz to 200 kHz, and even more typically between about 10 kHz and about 20 kHz, in one embodiment. The drive signals may each have a constant current, typically in the range of between 1-200 µA. and more typically about 5 µA, in one embodiment. The signal generator 120 may also generate signals involved in, for example, determining a location of the electrodes within the body of the patient, that may be utilized for mapping, navigation, and/or therapy delivery. The digital signal(s) generated by the signal source 120 are converted to analog signal(s) by D-to-A converter 110 and provided via filter 112 and switch 108 to selected bipolar electrodes. In response to the analog signals supplied between selected bipolar electrodes, a resulting voltage is measured at the electrode pairs by the switch 108, the filter 116, the A-to-D converter 114, and a synchronous demodulator circuit 122. In some embodiments, switch 108 selects the electrode to monitor in response to the excitation or drive signal delivered. The filter 116 and the A-to-D converter 114 convert the analog signal to a digital signal that can be operated on by the ECU 118. The synchronous demodulator circuit 122 isolates signals from one another based on the frequency of the excitation or drive signal, allowing a plurality of bipolar electrode pairs to be analyzed approximately simultaneously based on the plurality of excitation or drive signals supplied to the electrode pairs.

In some embodiments, the memory 126 may be configured to store data respective of the medical device 102, the patient, and/or other data (e.g., calibration data). Such data may be known before a medical procedure (medical device specific data, number of catheter electrodes, etc.), or may be determined and stored during a procedure. The memory 126 may also be configured to store instructions that, when executed by the processor 128 and/or a contact assessment module 124, cause the ECU 118 to perform one or more methods, steps, functions, or algorithms described herein. For example, but without limitation, the memory 126 may include data and instructions for determining contact status of the one or more electrodes based on one or measured electrical characteristics and may utilize the contact status of one or more electrodes to modify the contact status of neighboring electrodes. As discussed in more detail with respect to FIGS. 7A-12B, a determination that one or more electrodes are 'in contact' with tissue may be utilized to modify the contact status of neighboring electrodes. For example, in a simple case a determination that first and third electrodes are 'in contact' can be utilized to modify the 'no contact' status of a second electrode located between the first and third electrodes. In some embodiments, the contact assessment module 124 utilizes a processor executing instructions stored on the memory 126, an application specific integrated circuit (ASIC), or other type of processor. The ECU may be connected to a display 130, which may display an output of sensed tissue (e.g., heart), the medical device (not shown) and/or determined contact status of the one or more electrodes of the medical device 102. In some embodiments, this may include displaying the electrodes that were determined to be 'in contact' based on the sensed electrical characteristics and the electrodes that had their contact status modified based on the contact status of one or more neighboring electrodes. In other embodiments, only the final contact status of the electrodes is displayed, regardless of whether the contact status was modified by the contact status of one or more neighboring electrodes. In other embodiments, the display of contact status associated with each electrode is accompanied by a confidence level associated with the contact status. For example, an electrode that is determined to be 'in contact' with tissue based on the one or more measured electrical characteristics may have a higher confidence level associated with it than an electrode determined to be 'in contact' based on the contact status of one or more neighboring electrodes.

Figure 2:
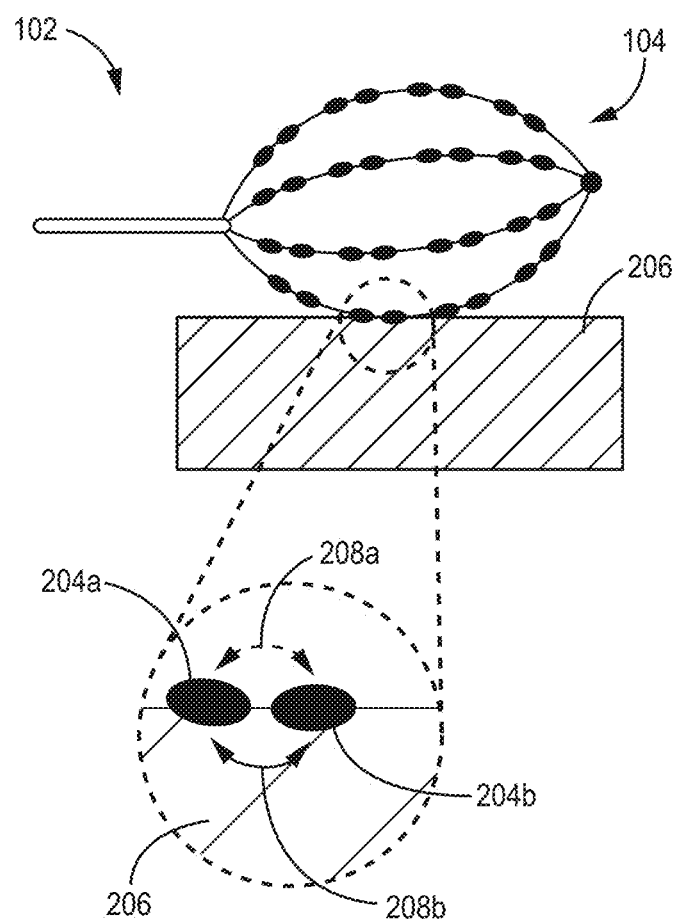
FIG. 2 is a diagrammatic depiction of a distal end of a medical device having a plurality of splines and a plurality of electrodes located on each spline according to some embodiments.

FIG. 2 is a diagrammatic depiction of a distal end 104 of a medical device 102 having a plurality of splines and a plurality of electrodes 204a. 204b located on each spline positioned adjacent cardiac tissue according to some embodiments. In some embodiments the contact status of the one or more electrodes 204a. 204b with the adjacent tissue 206 is determined based on one or more measured electrical characteristics. For example, in some embodiments a bipolar electrode complex impedance (BECI) measurement is utilized to determine the contact status of each of the plurality of electrodes. In the embodiment shown in FIG. 2, electrodes 204a and 204b form a bipolar electrode pair. A BECI measurement is generated by supplying an excitation signal to electrodes 204a and 204b, resulting in current flowing between the electrodes 204a and 204b as shown by dashed arrows 208a, 208b. The passage of at least a portion of the current 208a, 208b through the patient tissue 206 at the electrode-tissue interface affects the inductive, capacitive, and resistive effects of the electrode response to the drive signal(s). That is, the tissue contact affects the impedance measurements of the electrodes 204a. 204b. In general, if the electrodes 204a, 204b are not in contact with the tissue 206, then the circuit is formed within the blood pool of the patient and the BECI measurement decreases. If the circuit path includes tissue 206 as shown in FIG. 2, then the BECI measurement increases, reflecting the higher impedance of the tissue 206 as compared with measurements taken within the blood pool. BECI measurements are utilized to determine tissue contact status of the electrodes. In some embodiments, contact status may include a determination of 'in contact' or 'not in contact'. In other embodiments, contact status may include other contact status, such as intermittent contact, or a range of contact states. In other embodiments, other measured electrical characteristics may be utilized alone or in combination with the measured BECI values to determine contact status of each of the electrodes.

In other embodiments, the distal end 104 of the medical device 102 may incorporate a plurality of different geometries and/or designs. The embodiment shown in FIG. 2 includes a plurality of splines positioned in a basket geometry, wherein each spline includes a plurality of electrodes. The embodiment shown in FIG. 4 similarly includes a plurality of splines, each spline including only a single electrode. In other embodiments, the distal end of the medical device 202 is a grid-like array of electrodes shown in more detail in FIG. 3. In other embodiments, the distal end of the medical device may be curved or loop-like, with a plurality of electrodes spaced along the distal end. Likewise, a variety of different types, geometries, and sizes of electrodes may be utilized at the distal end of the medical device. For the sake of simplicity, modifying the contact status based on the contact status of one or more neighboring electrodes is described with respect to the grid-like array of electrodes shown in FIG. 3. However, it should be appreciated that modifying the contact status of electrodes may be applied to any geometry of electrodes utilized to determine contact status within a medical environment.

Figure 3:
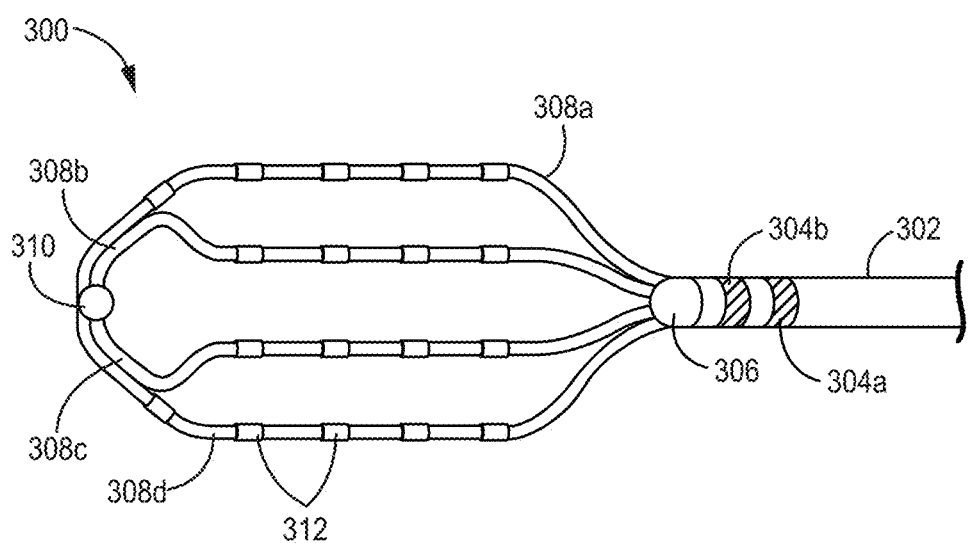
FIG. 3 is a diagrammatic depiction of a distal end of a medical device having a plurality of splines, each spline including a plurality of electrodes organized in a grid-like array according to some embodiments.

FIG. 3 is top view of a grid array catheter 300. In some embodiments, grid array catheter 300 includes a shaft 302, shaft electrodes 304a and 304b, a proximal end 306, a plurality of splines 308a, 308b, 308c. 308d, a distal end 310, and a plurality of spline electrodes 312. In some embodiments, electrical characteristics are measured at each of the plurality of electrodes and utilized to determine a contact status of the respective electrode. For example, in some embodiments, bipolar electrode complex impedance (BECI) measurements may be taken between any pair of adjacent electrodes and may be utilized alone or in combination with other measured electrical characteristics to determine a contact status of the electrode.

Figure 4:
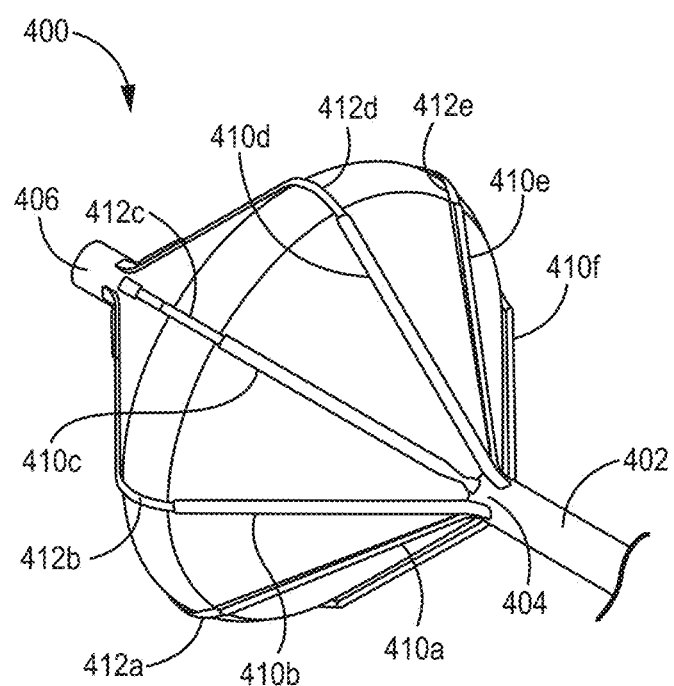
FIG. 4 is a diagrammatic depiction of a distal end of a medical device having a plurality of splines, each spline including a plurality of electrodes organized in a basket-like array according to some embodiments.

FIG. 4 is an isometric view of a basket catheter 400. In some embodiments, basket catheter 400 includes a shaft 402, a proximal end 404, a distal end 406, and a plurality of splines 410a-410f extending between the proximal end 404 and the distal end 406. Each of the plurality of splines 410a-410f includes a corresponding electrode 412a-412f. In some embodiments, electrical characteristics are measured at each of the plurality of electrodes-including for example BECI measurements—and utilized alone or in combination with one another to determine a contact status of the respective electrode.

Figure 5:
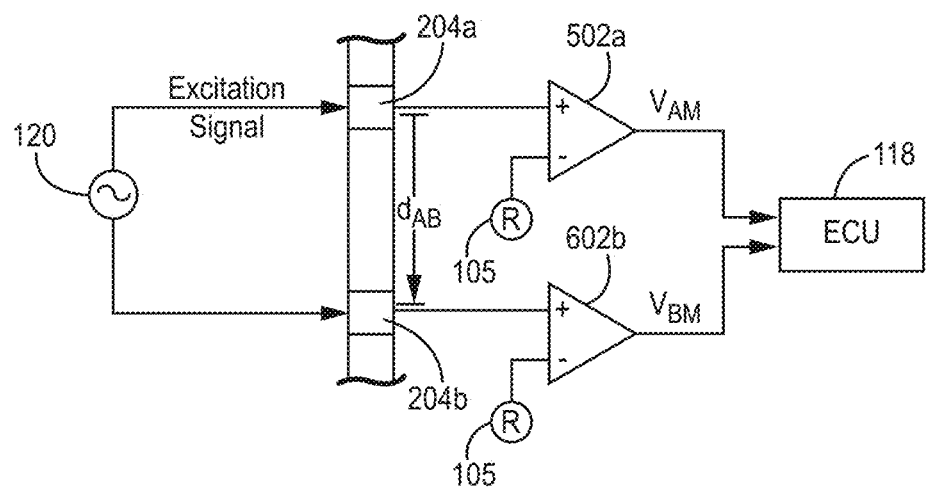
FIG. 5 is a diagrammatic view of components utilized to measure impedance between two electrodes located on the medical device according to some embodiments.

FIG. 5 is a circuit diagram illustrating the circuit elements utilized to excite the bipolar pair of electrodes and measure the resulting complex impedance according to some embodiments. In particular, the circuit diagram includes a signal source 120 (shown in FIG. 1), a pair of electrodes 204a, 204b (shown in FIG. 2), rust and second operational amplifiers 502a, 502b, and ECU 118 (also shown in FIG. 1). In some embodiments, the signal source 120 generates an excitation signal that is provided to first and second electrodes 204a. 204b. The first op-amp 502a includes a first terminal (e.g., positive terminal) connected to the first electrode 204a and a second terminal (e.g., negative terminal) connected to a reference electrode 105 (e.g., surface electrode). The output of the op-amp 502a reflects the difference in voltage between the first electrode 204a and the reference electrode 105. The second op-amp 502b includes a first terminal (e.g., positive terminal) connected to the second electrode 204b and a second terminal (e.g., negative terminal) connected to a reference electrode 105 (e.g., surface electrode). The output of the op-amp 502b reflects the difference in voltage between the second electrode 204b and the reference electrode 105. The respective outputs of the first op-amp 502a and the second op-amp 502b are provided to the ECU 118, which utilizes the respective measurements to determine the bipolar electrode complex impedance (BECI).

Figure 6:
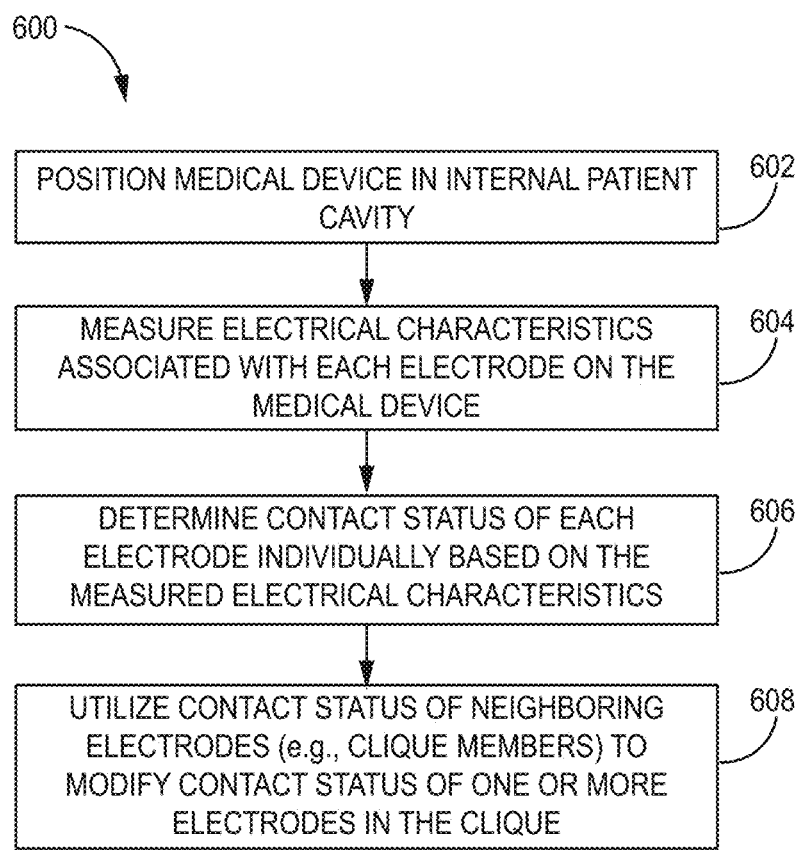
FIG. 6 is a flowchart illustrating steps utilized to determine contact status of electrodes located on a medical device using bipolar electrode complex impedance (BECI) measurements and the contact status of neighboring electrodes according to some embodiments.

FIG. 6 is a flowchart 600 illustrating steps utilized to modify contact status of one or more electrodes based on the contact status of one or more neighboring electrodes according to some embodiments. At step 602, a medical device, such as the device 102, can have a distal end positioned within a patient in an internal cavity. The distal end can include a plurality of electrodes as described above. As described above, various geometries may be utilized at the distal end of the medical device, including basket-shaped geometries, grid-like arrays of electrodes, curved splines, etc. At step 604, an electrical characteristic associated with each electrode is measured after the distal end of the medical device is inserted inside the patient. As also described above, the electrical characteristic can include an impedance measurement taken at an electrode or between two electrodes. In some embodiments, a bipolar electrode complex impedance (BECI) is measured between pairs of electrodes.

At step 606, a contact status of each electrode can be individually determined based on the measured electrical characteristic from step 604 for that particular electrode. In some embodiments, the contact status of each electrode is determined to be in contact or not in contact. In other embodiments, rather than a binary determination, a plurality of contact statuses may be utilized. For example, in one embodiment the contact statuses may be 'no contact', 'intermittent contact', and 'in contact'. In other embodiments, additional contact states may be utilized to convey various levels of contact between the electrode and the adjacent tissue. In some embodiments, step 606 can be performed by an ECU that is part of the system for the medical device.

At step 608, the contact status of the electrodes are analyzed in view of the contact status of neighboring electrodes, and in some cases, the contact status of those neighboring electrodes are utilized to modify the contact status of one or more electrodes. For the sake of simplicity, contact states are described as being modified to indicate a higher contact state (e.g., from a 'no contact' state to an 'in contact' state or from an 'intermittent contact' state to an 'in contact' state, although in other embodiments the reverse may also be true). At step 608, only those electrodes identified as something other than 'in contact' are analyzed to determine whether the contact state should be modified. That is, if an electrode has already been determined at step 606 to be 'in contact' with the tissue, then no analysis is required at step 608 to determine whether to modify the status of the electrode. It should be recognized however, that if the contact status of electrodes may be modified to indicate a lower level of contact (e.g., from 'in contact' to 'no contact') then at step 608 all electrodes would need to be analyzed in view of the contact status of their neighboring electrodes.

In some embodiments, the determination of whether to modify the contact status of an electrode is based, at least in part, on the contact status of one or more neighboring electrodes. In some embodiments, described in more detail with respect to FIGS. 7A-12B, one or more rules are applied regarding when to modify the contact status of a given electrode based on the contact status of one or more neighboring electrodes. In some embodiments, one or more additional inputs may be utilized, including for example, distance from an electrode being analyzed to one or more of the neighboring electrodes, contact status of the neighboring electrodes (if contact status includes more than a binary determination of 'in contact' or 'no contact'), contact status of the electrode being analyzed (if contact status includes more than a binary determination of 'in contact' or 'no contact'), and/or contact status history of the electrode being analyzed and/or of the one or more neighboring electrodes.

In some embodiments, the contact status of an electrode is modified based on the contact status of neighboring electrodes. The term neighboring may refer to electrodes both adjacent and non-adjacent to the electrode being analyzed for modification. In some embodiments, the plurality of electrodes are organized into sub-sets of electrodes referred to as cliques, wherein an electrode may be a member of one or more cliques and wherein the clique may be comprised of electrodes that are both adjacent and non-adjacent to one another. In some embodiments, the contact status of an electrode is modified based on the contact status of electrodes within a clique. For example, in some embodiments each clique is comprised of three electrodes that together define a plane. In some embodiments, the contact status of one of the electrodes in the clique may be modified from a 'no contact' state to a 'contact' state if the contact status of one or both of the other electrodes in the clique are determined at step 606 to be 'in contact'. As shown in the examples provided in FIGS. 7A-13B, a variety of methodologies may be utilized to determine whether to modify a contact status of an electrode based on the contact status of one or more neighboring electrodes, including for example one or more adjacent electrodes, one or more non-adjacent electrodes, and/or one or more electrodes included as part of a clique.

In some embodiments, changing the contact status of an electrode may include changing a contact status from 'no contact' to 'in contact'. In some embodiments, the contact status of the electrode may also be changed from 'in contact' to 'no contact' based on the contact status of neighboring electrodes. However, for the sake of simplicity the contact status in the examples provided are always modified from a lesser contact state to a greater contact state. In some embodiments, in which a plurality of contact states are possible, modification of a contact state may be based on a combination of physical distance/proximity of neighboring electrodes and contact status of neighboring electrodes. For example, immediately adjacent or closer-proximity electrodes may be given greater weight to modifying the contact status of an electrode. For example, the contact state of an electrode located immediately adjacent and between two electrodes determined at step 606 to be 'in contact' may have a contact state modified from 'no contact' to 'in contact' (despite an intermediate category of 'intermittent contact'). In some embodiments, the contact state of an electrode located between two electrodes indicated to be 'in contact', but not immediately adjacent to one or more of the electrodes, may have a contact state changed from 'no contact' to 'intermittent contact', rather than to 'in contact', as a result of the larger distance between the respective electrodes. In this example, the distance from the one or more electrodes indicated to be 'in contact' is utilized in conjunction with the contact status of the electrodes to determine whether to modify the contact status of a given electrode.

In some embodiments, a magnitude or value representative of the contact state may be utilized as an input in determining whether to modify a contact status. For example, in some embodiments an electrode may be assigned more states than simply 'in contact' and 'no contact'. In the simplest example, an electrode may also be assigned 'intermittent contact', but other embodiments may include a spectrum of possible contact states. In still other embodiments, actual value (e.g., BECI values, other calculations utilized to determine contact status) of neighboring electrodes and/or of the electrode being analyzed may be utilized to determine contact status. In these embodiments, the magnitude of the contact status associated with both the neighboring electrodes and the electrode being analyzed for modification may be utilized in the determination of whether to modify contact status and what the contact status should be modified to. For example, a plurality of neighboring electrodes determined based on measured electrical characteristics to be in very good contact with tissue may have a greater impact on determining whether to modify contact status than a plurality of neighboring electrodes determined based on measured electrical characteristics showing less confidence or certainty regarding contact. Likewise, the contact state (e.g., magnitude or value representative of contact state) of the electrode being analyzed for modification may be utilized as an input in determining whether to modify the contact state. For example, in a simplest case the modification of contact status may be limited to a single step (e.g., from 'no contact' to 'intermittent contact' or from 'intermittent contact' to 'in contact'). In other embodiments, the modification of contact status may be based on a combination of the contact status of the electrode being analyzed and the contact status of the neighboring electrodes.

In this way, at step 608, an electrode assigned an initial contact status (e.g., 'no contact') at step 606, based on measured electrical characteristics, may have that contact status changed based on the contact status of the neighboring electrodes.

Specific examples of rules that may be applied to change the contact status of an electrode are described below in reference to FIGS. 7A-11B. In these examples, it is assumed that measured electrical characteristics are utilized to assign each electrode a binary state of contact (e.g., 'in contact' or 'no contact') and that contact status is only changed from 'no contact' to 'in contact'. It should be appreciated that in other embodiments, various other factors described above may be utilized in conjunction with these rules to determine whether to modify contact status of a given electrode. For the sake of simplicity, a grid-like array of electrodes similar to that shown in FIG. 3 and having sixteen electrodes is utilized as an example. It should be understood that the principles discussed herein may be applied to other configurations of electrodes.

Figures 7A, 7B:
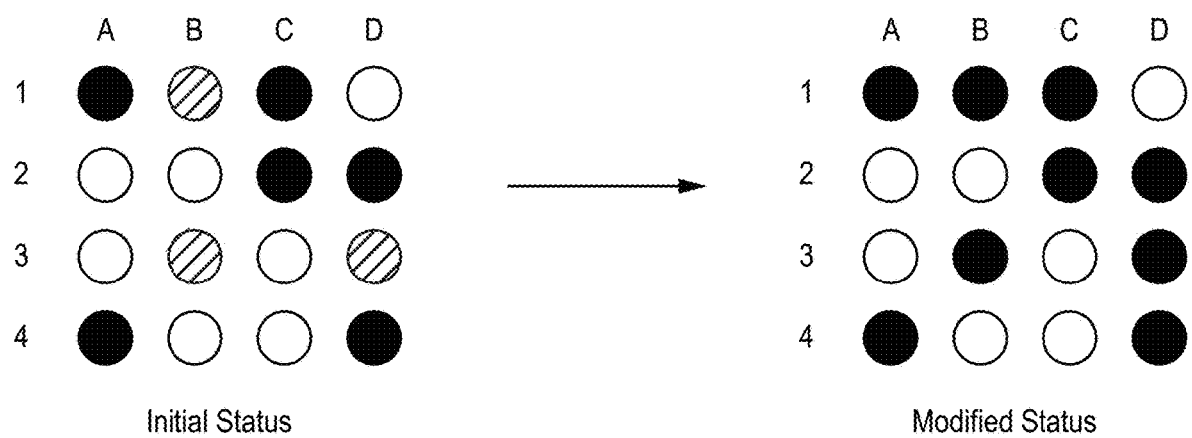
FIGS. 7A and 7B are diagrams illustrating a 4×4 electrode grid and the modification of electrode contact status for a clique based on the contact status of neighboring electrodes in the clique according to some embodiments.

FIG. 7A represents a 4×4 grid for a grid catheter, similar to the catheter 300 of FIG. 3, having 16 electrodes. The alpha-numeric labels for the electrodes are used here for ease of description. The initial determination of contact status (step 606 of FIG. 6) for the electrodes in the grid is shown in FIG. 7A based on one or more measured electrical characteristics. For the sake of simplicity, the status of electrodes indicated with white circles are not relevant to the analysis and so can be ignored (or assigned no contact values), gray circles represent electrodes determined to be 'no contact' based on the measured electrical characteristic, and black circles represents electrodes in a 'contact' state based on the measured electrical characteristic. FIG. 7B shows the modified state of the electrodes (step 608 of FIG. 6), with black circles utilized to indicate 'in contact'.

As shown in FIG. 7A, electrodes A1, C1, C2, D2, A4 and D4 were determined to be 'in contact' based on the measured electrical characteristic while electrodes B1, B3, D3: were assigned a 'no contact' state based on the measured electrical characteristic.

In the example shown in FIGS. 7A and 7B, the rule applied is that the contact status of an electrode can be modified from 'no contact' to 'in contact' if located between any pair of electrodes determined to be 'in contact'. As shown in FIGS. 7A and 7B, electrode B1 is modified from 'no contact' (gray in FIG. 7A) to 'in contact' (black in FIG. 7B) based on electrodes A1 and C1 being 'in contact'. Similarly, electrode B3 is modified based on electrodes C2 and A4 being 'in contact', and electrode D3 is modified based on electrodes D2 and D4 being 'in contact'. In some embodiments, the output displayed to a technician via a display would be based on the contact status shown in FIG. 7B.

In the particular example described above and shown in FIGS. 7A and 7B, the pair of electrodes that are determined as 'in contact' are separated by only one electrode, which is the electrode that can be modified from 'no contact' to 'in contact'. In some embodiments, the pair of electrodes can be separated by more than one electrode, and each electrode between the pair of electrodes can be modified based on the pair of electrodes. For example, if A1 and A4 are 'in contact', one or both of A2 and A3 can be modified from 'no contact' to 'in contact'; similarly, if A1 and D4 are 'in contact', one or both of B2 and C3 can be modified from 'no contact' to 'in contact'.

Figures 8A, 8B:
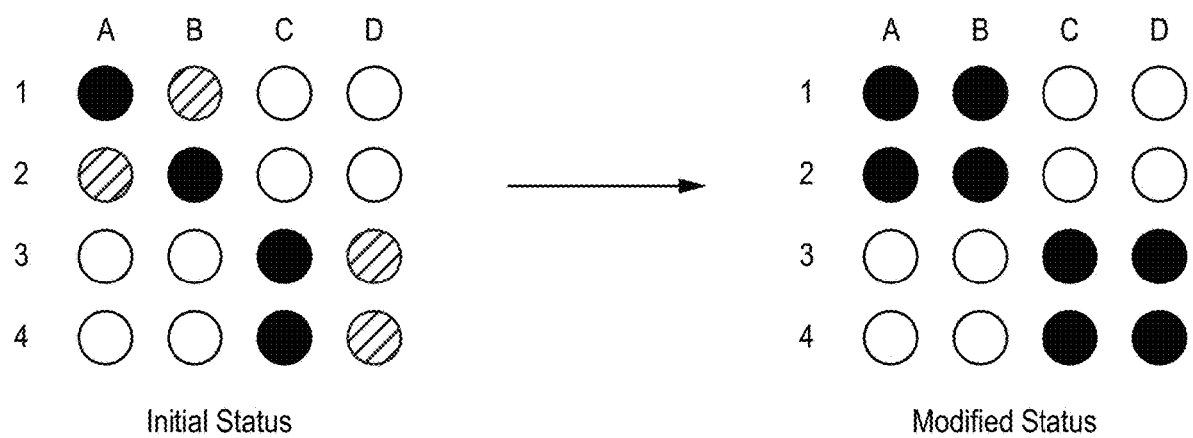
FIGS. 8A and 8B are diagrams illustrating a 4×4 electrode grid and the modification of electrode contact status for another clique (single square) based on the contact status of neighboring electrodes in the clique according to some embodiments.

FIGS. 8A and 8B illustrate the modification of electrode status based on the contact status of electrodes located within a 2×2 clique. As shown in FIG. 8A, electrodes A1, B2, C3, and C4 were determined to be 'in contact' based on the measured electrical characteristic. Electrodes A2, B1, D3 and D4 were determined to be 'no contact' based on the measured electrical characteristic. In this example, electrodes are organized into cliques comprised of four electrodes forming a square, and the rule applied is that if two or more electrodes within a given clique (e.g., 2×2 square) are identified as 'in contact' based on the measured characteristic then the other two electrodes in the square may have their contact status modified to 'in contact'. As shown in FIG. 8B, electrodes A2 and B1 are flipped or modified to 'in contact' state based on contact state of electrodes A1 and B2. Similarly, electrodes D3 and D4 are flipped from 'no contact' to 'in contact' based on the contact state of electrodes C3 and C4. In this example, it does not matter which electrodes within the grouping of electrodes or clique are 'in contact' so long as two of the four electrodes (in this example) indicate 'in contact', the other two can be flipped from 'no contact' to 'in contact'.

Figures 9A, 9B:
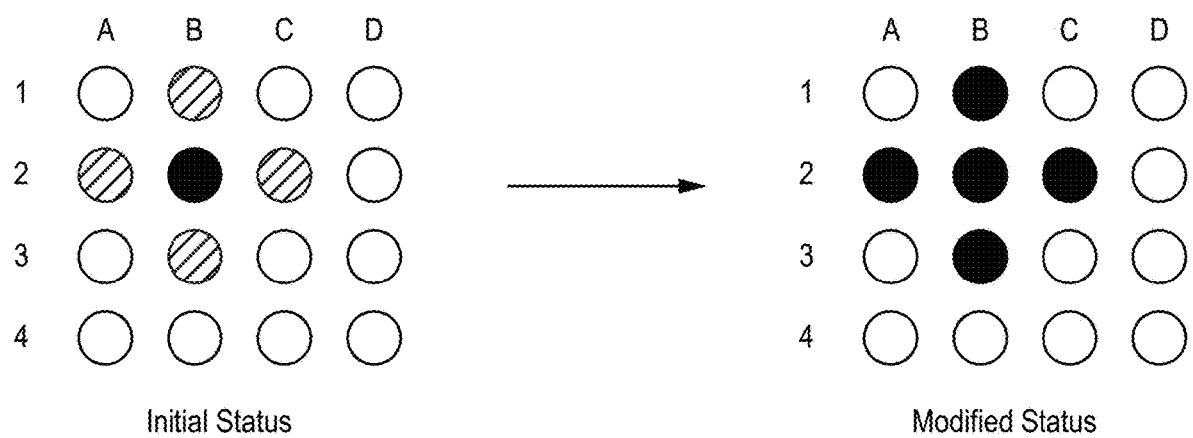
FIGS. 9A and 9B are diagrams illustrating a 4×4 electrode grid and the modification of electrode contact status for another clique (nearest neighbor) based on the contact status of neighboring electrodes in the clique according to some embodiments.

FIGS. 9A and 9B illustrate an example in which contact states are modified if located adjacent (horizontally, vertically) to an electrode determined to be 'in contact' with tissue. In this example, electrode B2 was determined to be 'in contact' based on the measured electrical characteristic (as shown in FIG. 9A). Application of the rule that contact states can be changed if an electrode is located adjacent (vertically, horizontally) to an electrode that is in contact results in electrodes B1, A2, C2 and B3 located adjacent to electrode B2 being modified from 'no contact' to 'in contact' as shown in FIG. 9B. In some embodiments, the contact status illustrated in FIG. 9B would be displayed to a user or technician.

Figures 10A, 10B:
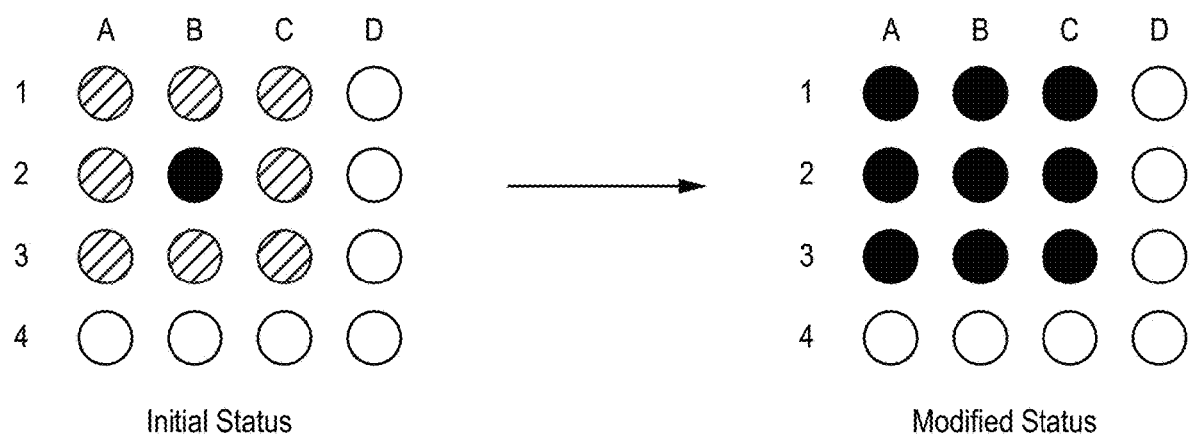
FIGS. 10A and 10B are diagrams illustrating a 4×4 electrode grid and the modification of electrode contact status for another 'nearest neighbor' clique based on the contact status of neighboring electrodes in the clique according to some embodiments.

FIGS. 10A and 10B illustrate an example similar in which contact states are modified if located adjacent (horizontally, vertically, diagonally) to an electrode determined to be 'in contact' with tissue. In this example, electrode B2 once again is determined to be 'in contact' based on the measured electrical characteristic (as shown in FIG. 10A). Application of the rule that contact states can be changed if an electrode is located adjacent (vertically, horizontally, diagonally) to an electrode that is in contact results in electrodes A1, B1, C1, A2, C2, A3, B3, and C3 located adjacent to electrode B2 being modified from 'no contact' to 'in contact' as shown in FIG. 10B. In some embodiments, the contact status illustrated in FIG. 10B would be displayed to a user or technician.

Figures 11A, 11B:
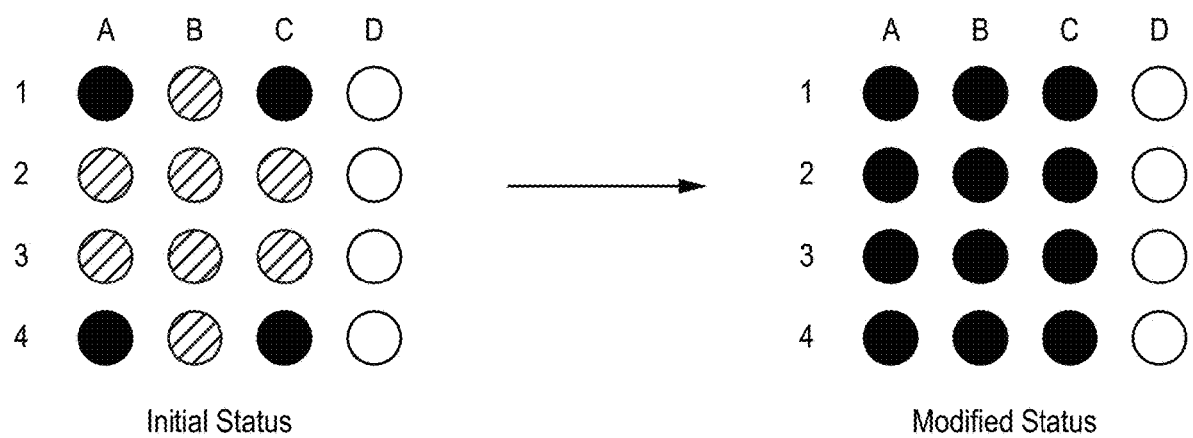
FIGS. 11A and 11B are diagrams illustrating a 4×4 electrode grid and the modification of electrode contact status for another clique (four corners) based on the contact status of neighboring electrodes in the clique according to some embodiments.

FIGS. 11A and 11B illustrate an example in which contact states are modified if located within a rectangle (or other shape) defined by electrodes determined to be 'in contact'. For example, in the embodiment shown in FIG. 11A, electrodes A1, C1, A4, and C4 are determined to be in contact based on measured electrical characteristics. Electrodes B1, A2, B2, C2, A3, B3, C3, and B4 are determined to not be in contact based on measured electrical characteristics. Electrodes A1, C1, A4, and C4 form a rectangle. In this example, application of the rule results in the contact states of electrodes B1, A2, B2, C2, A3, B3, C3, and B4 being modified to 'in contact' as shown in FIG. 11B because they are located within the rectangle defined by electrodes A1, C1, A4, and C4. In this example, some of the electrodes are located between electrodes determined to be in contact (for example electrode B1 is located between 'in contact' electrodes A1 and C1). Other electrodes, such as electrodes A2 and A3 are only located adjacent to one other electrode determined to be 'in contact'. In this example, electrodes A2 and A3 are modified to indicate contact because they are within the rectangle defined by electrodes A1, C1, A4, and C4 despite only being directly adjacent to one 'in contact' electrode. In some embodiments, the contact status illustrated in FIG. 11B would be displayed to a user or technician.

A 4×4 grid (16 electrodes) is used in FIGS. 7A-11B as an example. It is recognized that catheters having more or less electrodes can utilize the methods described herein for defining cliques and modifying the contact status or one or more electrodes based on the contact status of other electrodes in the same clique. In other examples, the grid can be larger or smaller. The grid does not have to be a square. Alterative size grids include but are not limited to 2×3, 3×2, 3×3, 3×4, 4×3, 4×5, 5×4 or 5×5.

Figures 12A, 12B:
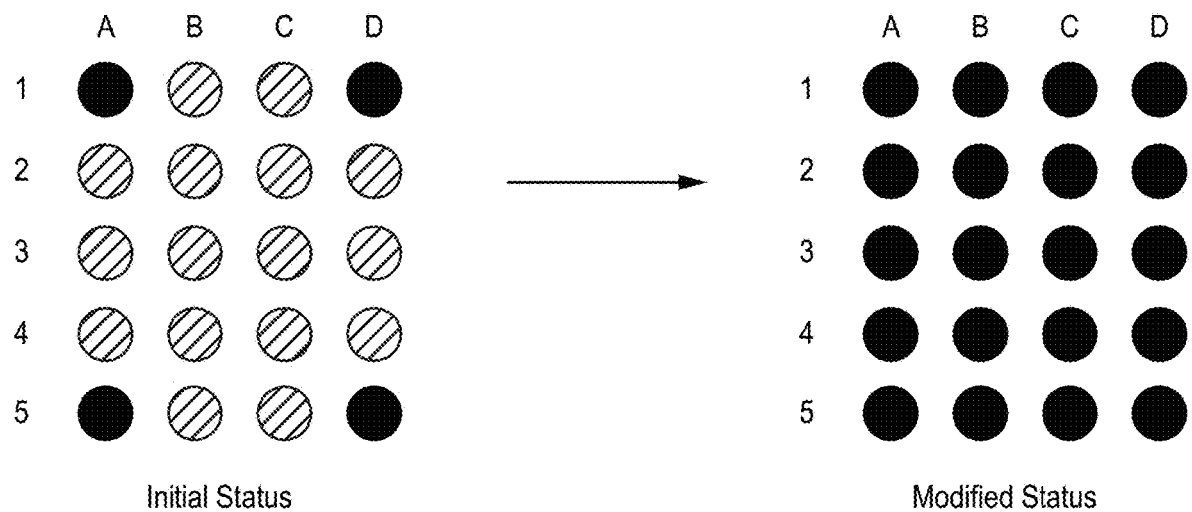
FIGS. 12A and 12B are diagrams illustrating a 5×4 electrode grid and the modification of electrode contact status for another 'four corners' clique based on the contact status of neighboring electrodes in the clique according to some embodiments.

In some examples, a neighboring electrode as defined herein is not necessarily an adjacent electrode. A non-adjacent electrode can be defined as a neighboring electrode if the non-adjacent electrode is within the same clique as the electrode in question. As an example, FIG. 12A shows a 5×4 grid with each of the outside corner electrodes (e.g., electrodes A1, D1, A5, and D5) determined to be 'in contact' based on the measured electrical characteristic. Applying the same rule as applied in FIGS. 11A and 11B, any electrode located within a rectangle defined by corners of the rectangle including electrodes determined to be 'in contact' can be modified to an 'in contact' state. Application of that rule to the example shown in FIG. 12A results in every electrode being changed to an 'in contact' state, including electrodes that are not adjacent to any electrode initially determined to be 'in contact'. For example, electrodes A3 and D3 are not immediately adjacent to any electrode initially determined to be 'in contact'.

The examples shown in FIGS. 7A-12B are merely illustrative of the types of rules that may be applied to change the state of one or more electrodes based on the contact status of one or more neighboring electrodes. A variety of other types of rules may be applied, either alone or in conjunction with other rules, depending on the application. In addition, although the examples shown in FIGS. 7A-12B were based on only two contact states (i.e., 'in contact' and 'no contact'), in other embodiments additional contact states may exist and those contact states may be utilized as an input to determine whether to modify the contact state of one or more neighboring electrodes. Likewise, the contact state of the electrode being analyzed (if not binary) may also be utilized as an input to determine the modified contact state of the electrode.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

Discussion of Possible Embodiments

The following are non-exclusive descriptions of possible embodiments of the present invention.

According to one aspect, a method of modifying contact status of one or more electrodes in a plurality of electrodes located on a medical device includes measuring an electrical characteristic of each electrode in the plurality of electrodes located on the medical device, determining a contact status for each electrode in the plurality of electrodes based on the measured electrical characteristic for the corresponding electrode, and modifying the contact status of a first electrode in the plurality of electrodes based on the determined contact status of one or more other electrodes in the plurality of electrodes.

The method of the preceding paragraph can optionally include, additionally and/or alternatively, any one or more of the following features, steps, configurations and/or additional components.

For example, the step of measuring the electrical characteristic may include measuring a bipolar electrode complex impedance (BECI).

The contact status may comprise a 'no contact' state and a 'contact' state.

The contact status may comprise a 'no contact' state, an 'intermittent contact' state, and a 'contact' state.

The step of modifying the contact status of the first electrode in the plurality of electrodes based on the determined contact status of one or more other electrodes in the plurality of electrodes may include changing a contact state of the first electrode from a 'no contact' state to a 'contact' state based on at least one adjacent electrode assigned a 'contact' state based on the measured electrical characteristic.

The step of modifying the contact status of the first electrode in the plurality of electrodes based on the determined contact status of one or more other electrodes in the plurality of electrodes may include changing a contact state of the first electrode from a 'no contact' state to a 'contact' state based on a pair of electrodes located on opposite sides of the first electrode being assigned a 'contact' state based on the measured electrical characteristic.

The step of modifying the contact status of a first electrode in the plurality of electrodes based on the determined contact status of one or more other electrodes in the plurality of electrodes may include changing a contact state of the first electrode from a 'no contact' state to a 'contact' state if any adjacent electrode is assigned a 'contact' state based on the measured electrical characteristic.

According to another aspect, a method of modifying contact status of one or more electrodes in a plurality of electrodes located on a medical device includes measuring an electrical characteristic of each electrode in the plurality of electrodes located on the medical device, determining a contact status for each electrode in the plurality of electrodes based on the measured electrical characteristic for the corresponding electrode, the contact status comprising 'in contact', 'intermittent contact' and 'no contact', and modifying the contact status of one or more electrodes in the plurality of electrodes based on one or more neighboring electrodes having a contact status of 'in contact'.

The method of the preceding paragraph can optionally include, additionally and/or alternatively any, one or more of the following features, steps, configurations and/or additional components.

For example, the step of modifying the contact status of one or more electrodes may include at least one of modifying the contact status of the one or more electrodes from 'no contact to 'in contact' and modifying the contact status of the one or more electrodes from 'intermittent contact' to 'in contact'.

The measured electrical characteristic may include a bipolar electrode complex impedance (BECI).

The one or more neighboring electrodes may include a pair of electrodes separated by one or more electrodes.

The one or more neighboring electrodes may include a nearest neighbor electrode in a lateral, vertical or diagonal direction.

The one or more neighboring electrodes may include four electrodes that form a rectangle separated by one or more electrodes.

According to another aspect, a system for use with a medical device having a plurality of electrodes and configured for insertion within a patient includes a signal generator configured to apply a plurality of drive signals across different pairs of electrodes of the medical device, a measurement circuit configured to measure responses of the plurality of electrodes to the drive signals and generate an impedance value for each of the plurality of electrodes of the medical device, and a contact assessment module configured to, for each electrode, determine a contact status of each of the plurality of electrodes based on the generated impedance value associated with each electrode, wherein the contact assessment module is further configured to modify the contact status of one or more of the plurality of electrodes based, at least, in part, on the contact status of one or more neighboring electrodes.

The system of the preceding paragraph can optionally include, additionally and/or alternatively any, one or more of the following features, steps, configurations and/or additional components.

For example, the contact status determined by the contact assessment module for each electrode may include a 'contact' state and a 'no contact' state.

The contact status determined by the contact assessment module for each electrode may include a 'contact' state, a 'no contact' state, and an 'intermittent contact' state.

Modification of the contact status by the contact assessment module may include changing a contact state of at least one of the electrodes from a 'no contact' state to a 'contact' state based on at least one neighboring electrode assigned a 'contact' state based on the measured electrical characteristic.

The invention claimed is:

1. A method of modifying contact status of one or more electrodes in a plurality of electrodes located on a medical device, the method comprising:
    measuring an electrical characteristic of each electrode in the plurality of electrodes located on the medical device;
    determining a contact status for each electrode in the plurality of electrodes based on the measured electrical characteristic for the corresponding electrode, wherein the contact status is indicative of contact of the corresponding electrode with adjacent tissue; and
    modifying the contact status of a first electrode in the plurality of electrodes based on the determined contact status of one or more other electrodes in the plurality of electrodes.

2. The method of claim 1, wherein measuring the electrical characteristic includes measuring a bipolar electrode complex impedance (BECI).

3. The method of claim 1, wherein the contact status comprises a 'no contact' state and a 'contact' state, wherein the 'no contact' state indicates that the electrode is not in contact with the adjacent tissue and wherein the 'contact' state indicates that the electrode is in contact with the adjacent tissue.

4. The method of claim 1, wherein the contact status comprises a 'no contact' state, an 'intermittent contact' state, and a 'contact' state.

5. The method of claim 1, wherein modifying the contact status of the first electrode in the plurality of electrodes based on the determined contact status of one or more other electrodes in the plurality of electrodes includes changing a contact state of the first electrode from a 'no contact' state to a 'contact' state based on at least one adjacent electrode assigned a 'contact' state based on the measured electrical characteristic.

6. The method of claim 1, wherein modifying the contact status of the first electrode in the plurality of electrodes based on the determined contact status of one or more other electrodes in the plurality of electrodes includes changing a contact state of the first electrode from a 'no contact' state to a 'contact' state based on a pair of electrodes located on opposite sides of the first electrode being assigned a 'contact' state based on the measured electrical characteristic.

7. The method of claim 1, wherein modifying the contact status of a first electrode in the plurality of electrodes based on the determined contact status of one or more other electrodes in the plurality of electrodes includes changing a contact state of the first electrode from a 'no contact' state to a 'contact' state when the first electrode is part of a rectangular formation of electrodes and the four electrodes in each of the corners of the rectangular formation are each assigned a 'contact' state based on the measured electrical characteristic.

8. A method of modifying contact status of one or more electrodes in a plurality of electrodes located on a medical device, the method comprising:
    measuring an electrical characteristic of each electrode in the plurality of electrodes located on the medical device;
    determining a contact status for each electrode in the plurality of electrodes based on the measured electrical characteristic for the corresponding electrode, the contact status indicative of contact of the corresponding electrode with adjacent tissue and comprising 'in contact', 'intermittent contact' and 'no contact'; and
    modifying the contact status of one or more electrodes in the plurality of electrodes based on one or more neighboring electrodes having a contact status of 'in contact'.

9. The method of claim 8, wherein modifying the contact status of one or more electrodes includes at least one of modifying the contact status of the one or more electrodes from 'no contact to 'in contact' and modifying the contact status of the one or more electrodes from 'intermittent contact' to 'in contact'.

10. The method of claim 8, wherein the measured electrical characteristic includes a bipolar electrode complex impedance (BECI).

11. The method of claim 8, wherein the one or more neighboring electrodes includes a pair of electrodes separated by one or more electrodes.

12. The method of claim 8, wherein the one or more neighboring electrodes includes a nearest neighbor electrode in a lateral, vertical or diagonal direction.

13. The method of claim 8, wherein the one or more neighboring electrodes are four electrodes that form a rectangle separated by one or more electrodes.

14. A system for use with a medical device having a plurality of electrodes and configured for insertion within a patient, the system comprising:
- a signal generator configured to apply a plurality of drive signals across different pairs of electrodes of the medical device;
- a measurement circuit configured to measure responses of the plurality of electrodes to the drive signals and generate an impedance value for each of the plurality of electrodes of the medical device; and
- a contact assessment module configured to, for each electrode, determine a contact status of each of the plurality of electrodes with adjacent tissue based on the generated impedance value associated with each electrode, wherein the contact assessment module is further configured to modify the contact status of one or more of the plurality of electrodes based, at least, in part, on the contact status of one or more neighboring electrodes.

15. The system of claim 14, wherein the contact status determined by the contact assessment module for each electrode includes a 'contact' state and a 'no contact' state.

16. The system of claim 14, wherein the contact status determined by the contact assessment module for each electrode includes a 'contact' state, a 'no contact' state, and an 'intermittent contact' state.

17. The system of claim 14, wherein modification of the contact status by the contact assessment module includes changing a contact state of at least one of the electrodes from a 'no contact' state to a 'contact' state based on at least one neighboring electrode assigned a 'contact' state based on the measured electrical characteristic.

18. The method of claim 1, wherein the contact status is indicative of whether there is direct contact of the corresponding electrode with adjacent tissue.

19. The method of claim 8, wherein the contact status is indicative of whether there is direct contact of the corresponding electrode with adjacent tissue.

20. The system of claim 14, wherein the determined contact status of each electrode is indicative of whether there is direct contact of that electrode with adjacent tissue.

\* \* \* \* \*